United States Patent [19]

Knab

[11] Patent Number: 4,764,344

[45] Date of Patent: Aug. 16, 1988

[54] DEVICE FOR THE DETERMINATION OF THE QUANTITATIVE COMPOSITION OF GASES

[75] Inventor: Hans-Josef Knab, Zürich, Switzerland

[73] Assignee: BBC Brown, Boveri & Company Ltd., Baden, Switzerland

[21] Appl. No.: 781,705

[22] Filed: Sep. 30, 1985

[30] Foreign Application Priority Data

Oct. 25, 1984 [CH] Switzerland .......................... 5100/84

[51] Int. Cl.⁴ ............................................. G01N 7/00
[52] U.S. Cl. ........................................ 422/89; 422/83; 436/178; 73/19
[58] Field of Search ............... 422/83, 89, 91, 101, 422/80, 81; 436/32, 177, 178, 181; 417/238; 55/189, 190, 314; 73/19

[56] References Cited

U.S. PATENT DOCUMENTS

| | | | |
|---|---|---|---|
| 2,391,390 | 12/1945 | Carlson | 422/83 |
| 3,116,999 | 1/1964 | Armbruster | 55/189 |
| 3,591,946 | 7/1971 | Loe | 55/189 |
| 4,207,450 | 6/1980 | Mittleman | 422/81 |
| 4,328,185 | 5/1982 | Reasons et al. | 422/82 |
| 4,333,952 | 6/1982 | McDonald | 568/335 |
| 4,340,391 | 7/1982 | Demaison et al. | 422/80 |
| 4,395,902 | 8/1983 | Espenscheid et al. | 73/19 |
| 4,402,211 | 9/1983 | Sugawara et al. | 73/19 |
| 4,409,814 | 10/1983 | Onuma et al. | |
| 4,411,157 | 10/1983 | Babin et al. | 436/177 |
| 4,444,040 | 4/1984 | Sakai et al. | 73/19 |
| 4,502,320 | 3/1985 | Sakai et al. | 73/23 |
| 4,580,309 | 4/1986 | Ogden | 15/302 |

FOREIGN PATENT DOCUMENTS

| | | | |
|---|---|---|---|
| 0017106 | 10/1980 | European Pat. Off. | |
| 2363111 | 3/1978 | France | |
| 32087 | 3/1978 | Japan | 73/19 |

OTHER PUBLICATIONS

Betriebsuberwachung durch Untersuchungen des Isolierols, pp. 211-215, 1977.

Primary Examiner—Barry S. Richman
Assistant Examiner—Jill Johnston
Attorney, Agent, or Firm—Burns, Doane, Swecker & Mathis

[57] ABSTRACT

A device used in the determination of the quantitative composition of gases dissolved in the insulating oil of oil-insulated electrical apparatus wherein the device is capable of removing insulating oil samples and includes a pump arrangement for the extraction of the gases from the insulating oil sample by means of reduced pressure and for conveying it to an analytical section is disclosed. This device is intended to operate directly on the electrical apparatus to be investigated. This is achieved in that the device is constructed in a transportable manner and incorporates a peristaltically operating pump arrangement. This pump arrangement contains at least one peristaltic pump, whose inlet can be connected via an extraction vessel with the removal device and whose outlet can be connected optionally with the outside air or with a gas collecting vessel. The gases from the gas collecting vessel are analyzed in the analytical section.

18 Claims, 3 Drawing Sheets

DEVICE FOR THE DETERMINATION OF THE QUANTITATIVE COMPOSITION OF GASES

BACKGROUND OF THE INVENTION

The present invention relates to a device for the determination of the quantitative composition of gases.

A device of this type for the determination of the composition of gases which uses the method of gas extraction from samples of insulating oil at reduced pressure to obtain the quantities of gas necessary for an analysis is already known from the publication "Betriesüberwachung durch Untersuchungen des Isolieröls" ("Plant monitoring by means of examinations of the insulating oil") by Dörnenburg and Hutzel (Elektrotechn. Z. A, vol. 98, 1977, pages 211 to 215).

In the device of the publication, before the actual sample of insulating oil is drawn off, a sufficient quantity of pre-rinse oil is extracted to ensure that the sample of insulating oil originates from the interior of the container of the electrical apparatus and not from supply lines and stopcocks. To avoid gas losses and adulteration due to external air foreign to the sample, the insulating oil sample is expediently drawn off in an evacuated sample container with air excluded. This sample container is then transported to a fixed laboratory, often over considerable distances.

In the laboratory the insulating oil is transferred from the sample container to a larger evacuated vessel, during which process gases dissolved in the insulating oil are liberated. These liberated gases are continuously pumped into a gas collecting vessel by means of a Toepler pump until the insulating oil is fully degassed. These gases are then analysed in a gas chromatograph.

In the above described process it proves to be disadvantageous that there are large distances between the point at which the insulating oil sample is removed and the fixed laboratory so that considerable waiting times must be expected before the analysis results are available. A portable gas detector is also known which permits the proportion of combustible gases in the gas cushion of an electrical apparatus filled with insulating oil to be determined. It is, however, not possible to determine the quantitative proportion of each gas component with this gas detector. In addition, it can be used only for apparatus having a gas cushion.

OBJECT AND SUMMARY OF THE INVENTION

It is in particular the object of the invention to provide a transportable device which, in a simple and safe manner, permits the quantitative composition of the gases dissolved in the insulating oil of electrical apparatus to be determined rapidly and reliably.

This object is accomplished by the device of this invention, which includes means for drawing a sample of the insulating oil, means for extracting gas from the oil sample and for collecting the gas, a gas chromatograph for the analysis of the gas, and a peristaltic pump for pumping the gas sample alternatively to the gas chromatograph or to the atmosphere.

The device according to the invention achieves the result that the quantitative composition of the gases dissolved in the insulating oil is determined on the spot within the shortest time. On the basis of these analysis results the condition of the oil insulation of the electrical apparatus under inspection is assessed with sufficient accuracy to make it possible to report on its operational reliability immediately.

It is further advantageous that the transport of insulating oil samples over long distances is as a rule no longer necessary, so that the risk of adulteration of the insulating oil sample with external air foreign to the sample is eliminated.

For valid measurement results this is accomplished by withdrawing relatively little insulating oil so that even measurement transducers which contain small quantities of insulating oil can be investigated without the operational reliability of the measurement transducer being endangered by the removal of the insulating oil.

In removing the oil sample the same quantity of insulating oil is always removed and degassed in the same interval of time. In this way very good comparative data are obtained for electrical apparatus filled with insulating oil which are routinely checked during their service life so that irregularities in the balance of gases must immediately be evident.

DESCRIPTION OF THE DRAWING

A preferred embodiment of this invention is illustrated in the accompanying drawings, in which.

DETAILED DESCRIPTION

Figure 1:
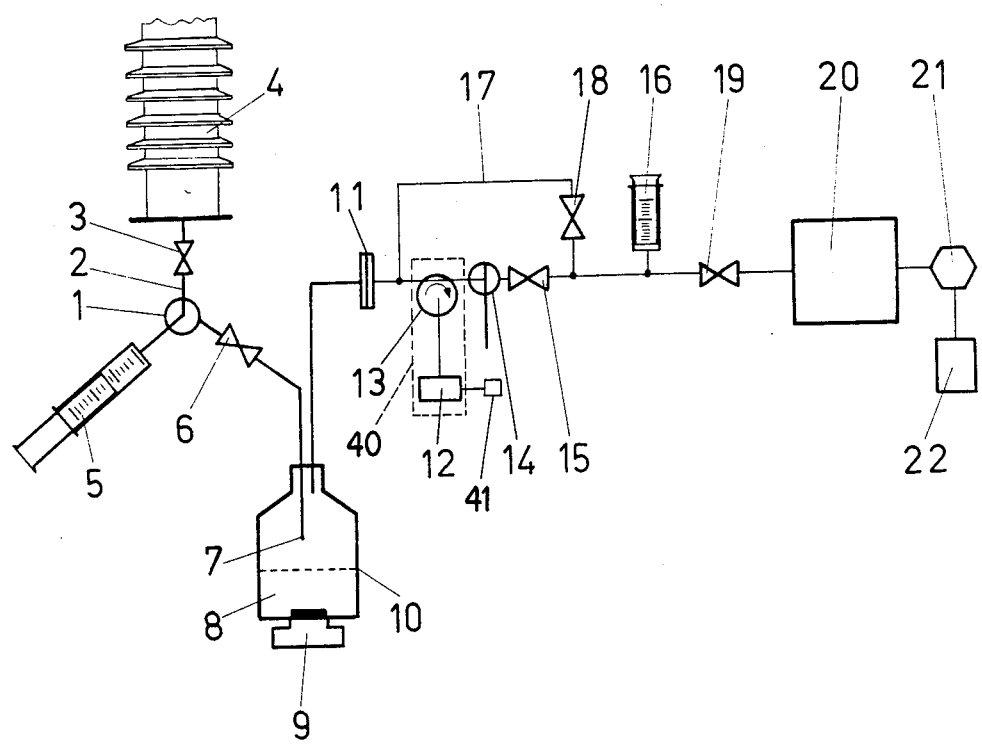
FIG. 1 is a schematic view of the apparatus of this invention.
Figure 2:
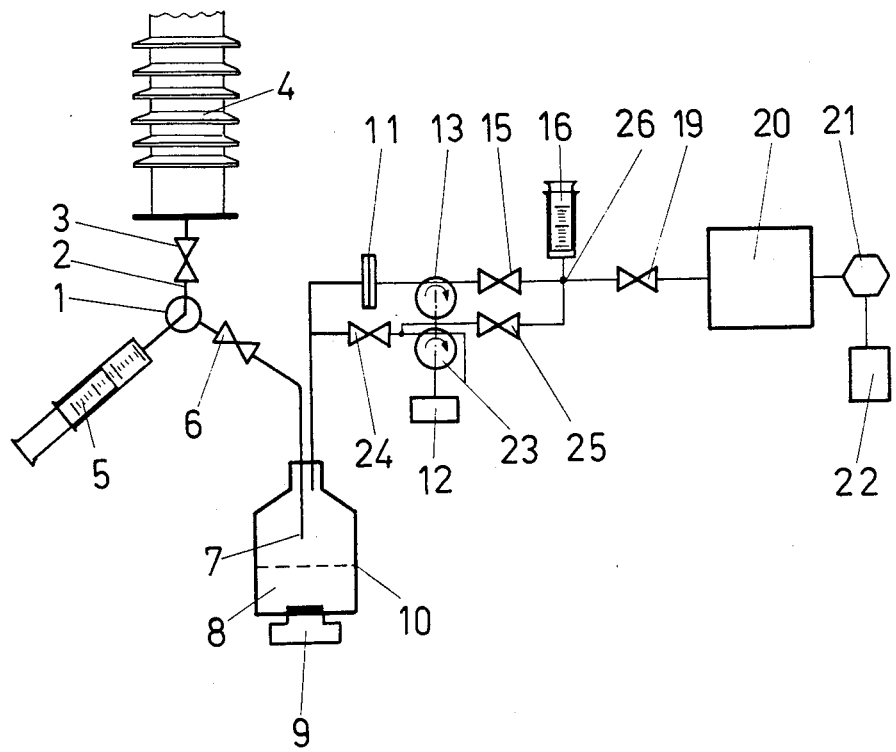
FIG. 2 is a modified form of the apparatus of FIG. 1.

Similar parts have been given the same reference numbers in FIG. 2 as in FIG. 1.

The device according to the invention as shown in FIG. 1 contains a changeover valve 1 whose inlet is connected in a pressure-sealed manner via a flexible piece of piping 2 to a drain valve 3 of an oil-insulated electrical apparatus 4 such as, for example, a current transformer for removing the insulating oil from the electrical apparatus 4. To one outlet of the changeover valve 1 is connected a pre-rinse syringe 5; the other outlet leads via a stopcock 6 through a jet nozzle 7 into a transparent extraction vessel 8. A stirrer 9, preferably a magnetic stirrer, is mounted in the base of the extraction vessel 8 on which a level mark 10 is provided on its side wall. From the extraction vessel 8 a pipe leads via an oil separating filter 11 to the inlet of a peristaltic pump 13 driven by a drive module 12. The outlet of the peristaltic pump 13 is connected to a changeover valve 14 which selectively connects the outlet of the peristaltic pump 13 to the outside air or to the inlet of a gas collecting vessel 16 via a stopcock 15. Between the inlet of the gas collecting vessel 16 and the inlet of the peristaltic pump 13 there is connected a bypass pipe 17 which can be opened or shut off by means of a stopcock 18. From the inlet of the gas collecting vessel 16 a further pipe runs via a stopcock 19 into a transportable gas chromatograph 20 which is connected to a flame ionization detector 21 and a chart recorder 22.

To explain the mode of operation FIG. 1 may be examined in more detail. With the stopcock 6 closed and the drain valve 3 open a sufficient quantity of pre-rinse oil is extracted from the electrical apparatus 4 with the pre-rinse syringe 5. The section between the closes stopcocks 6 and 19 is evacuated by the peristaltic pump 13, and while this is being done the outlet of the peristaltic pump 13 is connected to the outside air via the changeover valve 14; the stopcock 15 is closed and the stopcock 18 is open.

After a pumping time of, for example, 30 minutes a final pressure of 100 to 500 Pa is reached. The changeover valve 14 is changed to connect the pump 13 to the stopcock 15, the stopcock 15 is opened and the stopcock 18 closed. After the changeover valve 1 has been changed over to connect the drain valve 3 to the stopcock 6 and the stopcock 6 has been opened, an insulating oil flows from the container interior of the electrical apparatus 4 to the extraction vessel 8. On entering the extaction vessel 8 the insulating oil is sprayed through the jet nozzle 7. The gases dissolved in the insulating oil are extracted and pumped by the peristaltic pump 13 through the oil separating filter 11, which prevents the entry of whirled-up oil particles into the peristaltic pump 13, into the gas collecting vessel 16. When the level mark 10 is reached, the supply of further insulating oil is prevented by closing the stopcock 6. During the extraction, the insulating oil is circulated in the extraction vessel by a stirrer 9. The pumping process is discontinued after, for example, 10 minutes if the predominant part of the extracted gases is in the gas collecting vessel 16, and the stopcock 15 is closed. The prerinse oil is pressed back into the electrical apparatus 4 by means of the pre-rinse syringe 5 through the appropriately set changeover valve 1 and the drain valve 3.

After the stopcock 19 has been opened, the gas mixture passes from the gas collecting vessel 16 into the gas chromatograph 20 and is analyzed using the flame ionization detector 21. The analytical results are recorded by the recorder 22.

The device according to the modified form of the invention in FIG. 2 differs from that in FIG. 1 in that two trains of pipes connected together on the inlet side each lead to a peristaltic pump 13, 23. The first peristaltic pump 13 has an oil separating filter 11 inserted in front of it, while its outlet leads via a stopcock 15 to a pipe junction 26. The inlet of the second peristaltic pump 23 has a stopcock 24 inserted in front of it, while its outlet is connected to the outside air. The inlet of the second peristaltic pump 23 is connected to the pipe junction 26 via a connectpipe which can be shut off. A gas collecting vessel 16 and an inlet to a stopcock 19 are additionally connected to the pipe junction 26. The two peristaltic pumps 13, 23 are driven by a common drive module 12 via a common shaft.

The mode of operation of the device in FIG. 2 is similar to that of the device in FIG. 1. During the evacuation of the section between the closed stopcocks 6 and 19 the stopcocks 15, 24 and 25 are open. After a pumping time of, for example, 10 minutes a final pressure of 100 to 500 Pa is reached, and the stopcocks 24 and 25 are closed. This advantageously short pumping time compared with the arrangement in FIG. 1 is achieved as a result of the fact that during the evacuation process the oil separating filter 11 is partially bypassed. After the stopcock 6 is opened, an insulating oil flows, as already described, into the extraction vessel 8. The peristaltic pump 13 conveys the extracted gas into the gas collecting vessel 16. After completion of the extraction the stopcock 15 is closed. After the stopcock 19 is opened, the analysis of the gas mixture present in the gas collecting vessel 16 takes place, as already described.

If the device is designed for a lower final pressure, then, in either the device of FIG. 1 or that of FIG. 2 instead of one peristaltic pump two or more peristaltic pumps can be fitted in series.

Figure 3:
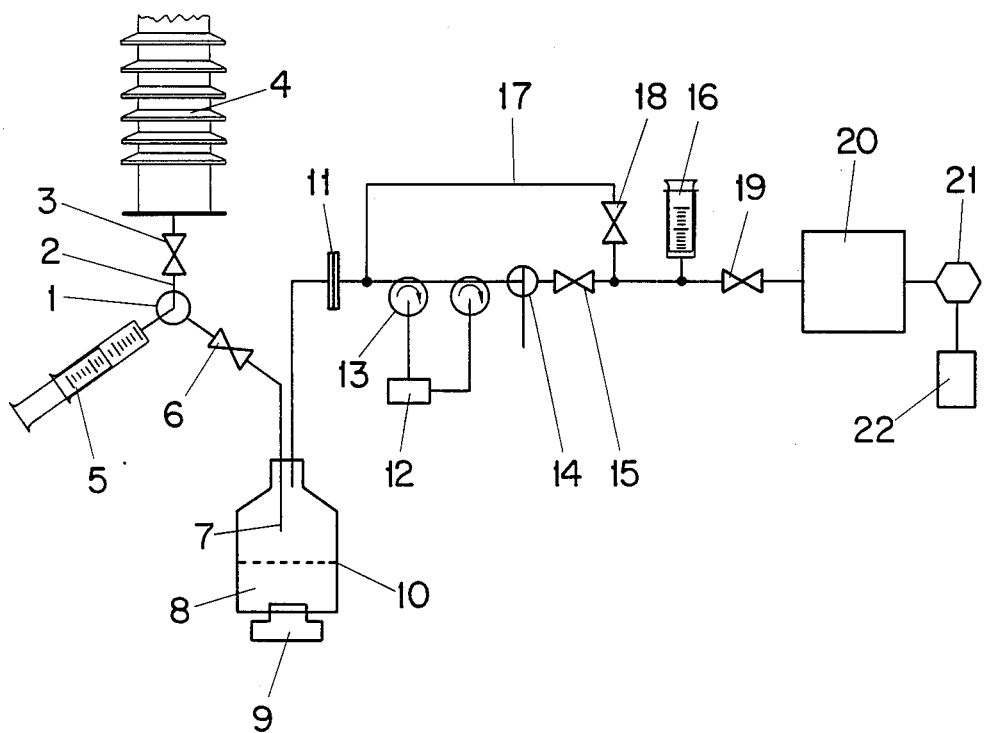
FIG. 3 shows a third exemplary embodiment of the invention.

Another modified form of the invention is shown in FIG. 3. This embodiment is simliar to the embodiment shown in FIG. 1, although it includes a second pump mounted in series with the first peristaltic pump 13. The second pump is also driven by the drive module 12.

In the case of oil-insulated electrical apparatus having a gas cushion above the oil filling, the gas mixture can be removed directly with air excluded and pumped into the gas collecting vessel; from there it passes, as already depicted, into the gas chromatograph for analysis. Further, this device can also be used to remove insulating oil samples if a suitable sample holder is used instead of the extraction vessel.

The device according to the invention is portable, accommodated for ready use and protected against transportation damage in one or more case-like housing 40. In the housings covers with rapid closures are provided over the operating apertures. The electrical energy needed for the operation of the device is drawn from batteries (not shown) which are mounted in an interchangeable manner in the housing making the device self-sufficient.

The device can be designed for remote control. This can be achieved in that the pre-rinse syringe is replaced by a remote-controllable electric pump, that a further additional pump pumps the gases from the gas collecting vessel into the gas chromatograph, and that the peristaltic pumps are constructed to be capable of remote-control operation by a remote control device 41. Each of the stopcocks can further be fitted with a remote-controlled electromagnetic actuator. In this way it is possible to monitor the condition of the insulating oil without having to take the electrical apparatus concerned out of service and without the measuring staff having to be stationed in the immediate vicinity of the electrical apparatus concerned during the measurement using the device.

While this invention has been described in accordance with the preferred embodiments of the invention, it is recognized that variations and changes may be made therein without departing from the invention as set forth in the claims.

What is claimed is:

1. In an apparatus for the determination of the quantitative composition of gases which are dissolved in insulating oil of an oil-insulated electrical apparatus, including a device for removing insulating oil samples from an oil-insulated electrical apparatus, a gas collecting vessel, a gas extraction section constructed and arranged for extraction of gases from the insulating oil samples supplied by the removing device by means of reduced pressure and for conveying extracted gases to the gas collecting vessel, and a gas chromatograph positioned and arranged for analysis of gases from the gas collecting vessel, the improvement comprising:
   a peristaltic pump whose inlet is connected via the gas extraction section to the removing device;
   means for selectively connecting an outlet of the peristaltic pump to either a vent to outside air or to an inlet of the gas collecting vessel; and
   a bypass pipe connected between the inlet of the pump and the inlet of the gas collecting vessel, said bypass pipe including a shut off valve.

2. The apparatus according to claim 1, wherein an oil separating filter is in fluid communication with the inlet of the peristaltic pump.

3. The apparatus according to claim 1, wherein a changeover valve is disposed with an inlet in communication with the outlet of the peristaltic pump and has outlets positioned and arranged in communication with the gas collecting vessel and with a vent to outside air; and a stopcock is inserted between the changeover valve and the gas collecting vessel.

4. The apparatus according to claim 1, wherein a second peristaltic pump is connected in series with the first peristaltic pump.

5. The apparatus according to claim 1, wherein the peristaltic pump is constructed for remote control operation.

6. The apparatus according to claim 1, wherein the peristaltic pump is installed in a case-like housing.

7. In an apparatus for the determination of the quantitative composition of gases which are dissolved in insulating oil of an oil-insulated electrical apparatus, including a device for removing insulating oil samples from an oil-insulated electrical apparatus, a gas collecting vessel, a gas extraction section constructed and arranged for extraction of gases from insulating oil samples supplied by the removing device by means of reduced pressure and for conveying extracted gases to the gas collecting vessel, and a gas chromatograph positioned and arranged for analysis of gases from the gas collecting vessel, the improvement comprising:
first and second peristaltically operating pumps whose inlets are connected via the gas extraction section to the removing device;
an outlet of the first peristaltic pump being connected to the inlet of the second peristaltic pump and to the gas collecting vessel,
means for selectively blocking the outlet of the first peristaltic pump,
an outlet of the second peristaltic pump being connected to a vent to outside air, and
means for selectively blocking the inlet of the second peristaltic pump.

8. The apparatus according to claim 7, wherein the first and second peristaltic pumps are mounted on a common drive shaft.

9. The apparatus according to claim 7, wherein an oil separating filter is in fluid communication with the inlet of the first peristaltic pump.

10. The apparatus according to claim 7, wherein a first stopcock is provided between the outlet of the first peristaltic pump and the gas collecting vessel, and a second stopcock is provided between the gas collecting vessel and the inlet of the second peristaltic pump, and a third stopcock is provided between the extraction vessel and the inlet of the second peristaltic pump.

11. An apparatus for determining the quantitative composition of gases which are dissolved in insulating oil of oil-insulated electrical equipment, comprising:
a gas collection vessel,
an extraction vessel,
first conduit means for conducting insulating oil from oil-insulated electrical equipment to said extraction vessel,
second conduit means for conducting gas from said extraction vessel to said gas collection vessel,
peristaltic pump means for pumping gas from said extraction vessel and said gas collection vessel and said second conduit,
first valve means in the second conduit for selectively conducting gas from said peristaltic pump means to the atmosphere or to said gas collection vessel,
gas chromatograph means for receiving gas from said gas collection vessel for analysis of the gas,
a bypass pipe connected between the inlet of the peristaltic pump means and the inlet of the gas collecting vessel, and
second valve means in the bypass pipe for shutting off flow in said bypass pipe,
wherein when said first and said second valve means are set in a first mode, the peristaltic pump means pumps gases from said extraction vessel, said gas collection vessel, and said second conduit to the atmosphere, and when said first and said second valve means are set in a second mode, said peristaltic pump means pumps gases from said extraction vessel to said gas collection vessel.

12. The apparatus as in claim 11 wherein the inlet of the peristaltic pump is in fluid communication with an oil separating filter.

13. The apparatus as in claim 11, including a changeover valve and a stopcock positioned and arranged after the changeover valve, said valve and stopcock disposed between an outlet of the peristaltic pump and the gas collection vessel.

14. The apparatus as in claim 11, wherein the peristaltic pump means is constructed for remote control operation.

15. The apparatus as in claim 11, wherein the peristaltic pump means is installed in a case-like housing.

16. An appartus for determining the quantitative composition of gases which are dissolved in insulating oil of oil-insulated electrical equipment comprising:
a gas collection vessel,
an extraction vessel,
first conduit means for conducting insulating oil from oil-insulated electrical equipment to said extraction vessel,
second conduit means for conducting gas from said extraction vessel to said gas collection vessel,
peristaltic pump means for pumping gas from said extraction vessel and said gas collection vessel and said second conduit,
valve means in the second conduit for selectively conducting gas from said peristaltic pump means to the atmosphere or to said gas collection vessel, and
gas chromatograph means for receiving gas from said gas collection vessel for analysis of the gas,
wherein the peristaltic pump means includes first and second peristaltic pumps whose inlets are connected to the extraction vessel, an outlet of the first peristaltic pump being connected to the inlet of the second peristaltic pump and to the gas collecting vessel, means for selectively blocking the outlet of the first peristaltic pump, the outlet of the second peristaltic pump being connected to a vent to outside air, and means for selectively blocking the inlet of the second peristaltic pump.

17. The apparatus as in claim 16 wherein the inlet of one of the peristaltic pumps is in fluid communication with an oil separating filter.

18. The apparatus in claim 16, wherein a first stopcock is provided between the outlet of the first peristaltic pump and the gas collecting vessel, a second stopcock is provided between the gas collecting vessel and the inlet of the second peristaltic pump, and a third stopcock is provided between the extraction vessel and the inlet of the second peristaltic pump.

* * * * *